(12) United States Patent
Stinauer et al.

(10) Patent No.: US 10,888,706 B2
(45) Date of Patent: Jan. 12, 2021

(54) EXTERNAL CHARGER FOR AN IMPLANTABLE MEDICAL DEVICE HAVING A THERMAL DIFFUSER (71) Applicant: Boston Scientific Neuromodulation Corporation, Valencia, CA (US)

(72) Inventors: Robert J. Stinauer, Valencia, CA (US); Joey Chen, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 132 days.

(21) Appl. No.: 15/938,325

(22) Filed: Mar. 28, 2018

(65) Prior Publication Data
US 2018/0345025 A1 Dec. 6, 2018

Related U.S. Application Data (60) Provisional application No. 62/514,304, filed on Jun. 2, 2017.

(51) Int. Cl.
A61N 1/378 (2006.01)
H02J 7/02 (2016.01)
H02J 7/00 (2006.01)
H02J 50/12 (2016.01)
H02J 50/90 (2016.01)
H01F 27/28 (2006.01)
H01F 38/14 (2006.01)
H05K 1/02 (2006.01)
(Continued)

(52) U.S. Cl.
CPC ....... A61N 1/3787 (2013.01); H01F 27/2876 (2013.01); H01F 38/14 (2013.01); H02J 7/0091 (2013.01); H02J 7/007192 (2020.01); H02J 7/025 (2013.01); H02J 50/12 (2016.02); H02J 50/90 (2016.02); H05K 1/0203 (2013.01); H05K 1/181 (2013.01); H05K 7/1427 (2013.01); A61N 1/37229 (2013.01); H05K 2201/1003 (2013.01); H05K 2201/10151 (2013.01)

(58) Field of Classification Search
CPC .......................... A61N 1/3787; A61N 1/3718; H01F 27/2876; H01F 38/14
See application file for complete search history.

(56) References Cited

U.S. PATENT DOCUMENTS 6,516,227 B1  2/2003  Meadows et al.
6,894,456 B2  5/2005  Tsukamoto et al.
(Continued)

OTHER PUBLICATIONS

US 9,601,939 B2, 03/2017, Cong et al. (withdrawn)
(Continued)

Primary Examiner — Joseph M Dietrich
(74) Attorney, Agent, or Firm — Lewis & Reese, PLLC (57) ABSTRACT An external charging system for an Implantable Medical Device (IMD) is disclosed having a thermal diffuser proximate to the primary charging coil for distributing heat from the primary charging coil. In an example, the primary charging coil is mounted to a first side of a circuit board, and the thermal diffuser is also connected to the first side and in contact with the primary charging coil. In one example, the thermal diffuser is a plastic material, such as an acrylic pad, with a high thermal conductivity and a low electrical conductivity. The thermal diffuser may also contact temperature sensors mounted to the first side of the circuit board.

20 Claims, 7 Drawing Sheets (51) Int. Cl.
*H05K 1/18* (2006.01)
*H05K 7/14* (2006.01)
*A61N 1/372* (2006.01)

(56) References Cited

U.S. PATENT DOCUMENTS

| | | | |
|---|---|---|---|
| 7,225,032 B2 | 5/2007 | Schmeling et al. | |
| 7,286,880 B2 | 10/2007 | Olson et al. | |
| 7,486,048 B2 | 2/2009 | Tsukamoto et al. | |
| 7,515,967 B2 | 4/2009 | Phillips et al. | |
| 7,979,126 B2 | 7/2011 | Payne et al. | |
| 8,005,547 B2 | 8/2011 | Forsberg et al. | |
| 8,321,029 B2 | 11/2012 | Aghassian | |
| 8,554,322 B2 | 10/2013 | Olson et al. | |
| 8,725,262 B2 | 5/2014 | Olson et al. | |
| 8,887,619 B2 | 11/2014 | Kallmyer et al. | |
| 9,002,445 B2 | 4/2015 | Chen | |
| 9,463,324 B2 | 10/2016 | Olson et al. | |
| 9,537,344 B2 | 1/2017 | Thompson et al. | |
| 2005/0075694 A1* | 4/2005 | Schmeling | A61N 1/3787 607/61 |
| 2006/0249714 A1 | 11/2006 | Hiroshige et al. | |
| 2007/0096686 A1* | 5/2007 | Jimenez | H02J 50/10 320/108 |
| 2011/0004278 A1 | 1/2011 | Aghassian et al. | |
| 2011/0234155 A1 | 9/2011 | Chen et al. | |
| 2013/0197608 A1 | 8/2013 | Eiger | |
| 2014/0025140 A1 | 1/2014 | Lui et al. | |
| 2015/0100109 A1* | 4/2015 | Feldman | A61N 1/3787 607/60 |
| 2015/0231392 A1 | 8/2015 | Fell et al. | |
| 2017/0361111 A1 | 12/2017 | Stouffer | |
| 2017/0361113 A1 | 12/2017 | Aghassian et al. | |
| 2017/0361114 A1* | 12/2017 | Aghassian | A61N 1/36142 |
| 2017/0361115 A1* | 12/2017 | Aghassian | A61N 1/37229 |
| 2017/0361116 A1* | 12/2017 | Aghassian | A61N 1/36142 |
| 2017/0361117 A1* | 12/2017 | Aghassian | A61N 1/37229 |

OTHER PUBLICATIONS

"Energy Storage: Phase Change Materials for Thermal Energy Storage," ClimateTechWiki, obtained on Apr. 25, 2017, 6 pages, retrieved from <http://www.climatetechwiki.org/technology/jiqwebpcm0>.

Invitation to Pay Additional Fees regarding corresponding PCT Application No. PCT/US2018/026514, dated Jul. 4, 2018.

* cited by examiner

EXTERNAL CHARGER FOR AN IMPLANTABLE MEDICAL DEVICE HAVING A THERMAL DIFFUSER

CROSS REFERENCE TO RELATED APPLICATIONS

This is a non-provisional application based on U.S. Provisional Patent Application Ser. No. 62/514,304, filed Jun. 2, 2017, which is incorporated herein by reference, and to which priority is claimed.

FIELD OF THE INVENTION

The present invention relates to wireless external chargers for use in implantable medical device systems.

INTRODUCTION

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

Figure 1A:
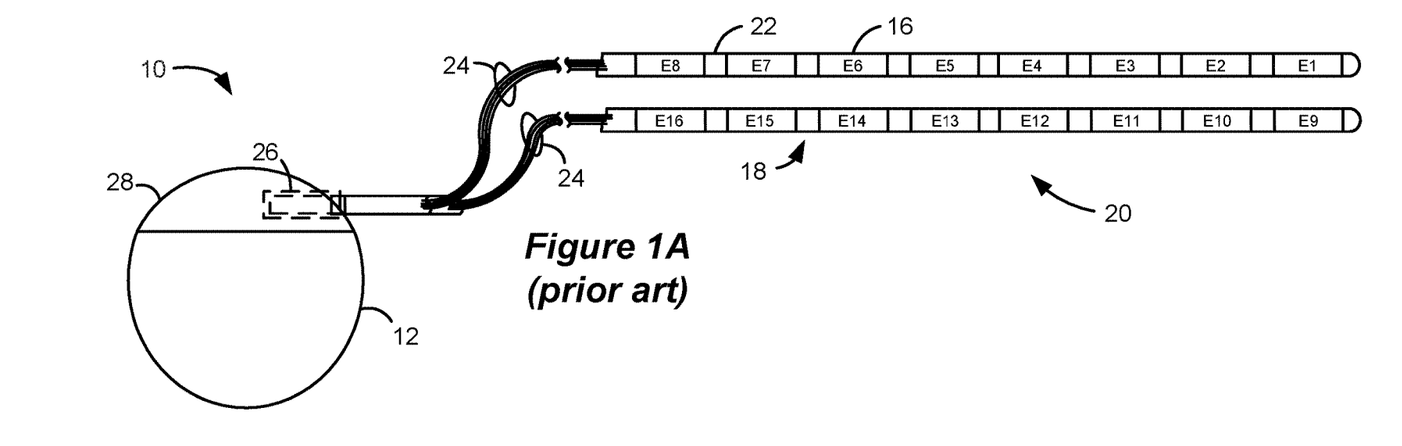
FIGS. 1A-1C show different views of an implantable pulse generator, a type of implantable medical device (IMD), in accordance with the prior art.
Figure 1B:
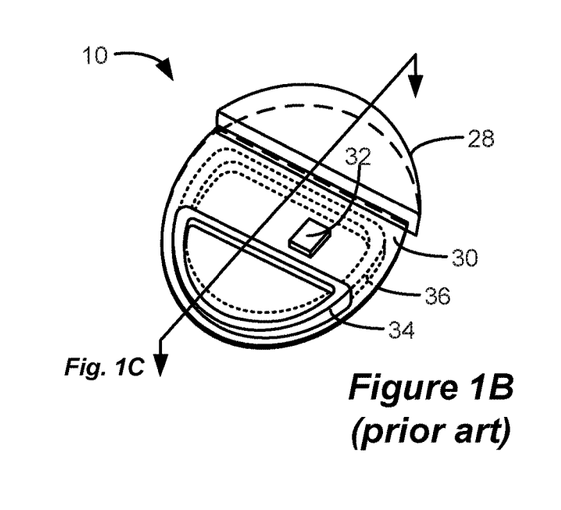
Figure 1C:
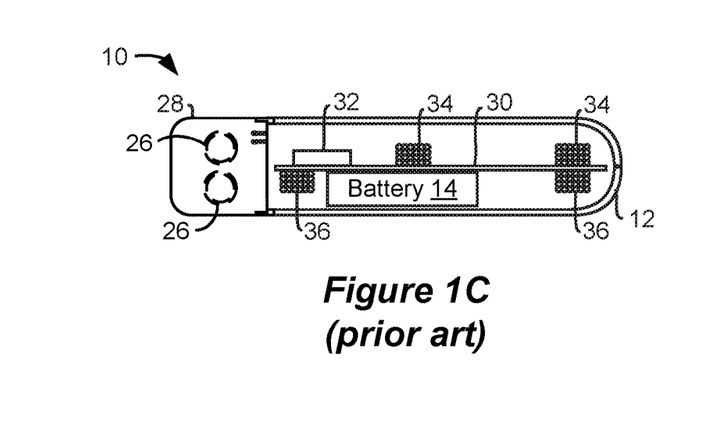

As shown in FIGS. 1A-1C, a SCS system typically includes an Implantable Pulse Generator (IPG) 10 (Implantable Medical Device (IMD) 10 more generally), which includes a biocompatible device case 12 formed of a conductive material such as titanium for example. The case 12 typically holds the circuitry and battery 14 (FIG. 1C) necessary for the IMD 10 to function, although IMDs can also be powered via external RF energy and without a battery. The IMD 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ex) on each lead 18, although the number of leads and electrodes is application specific and therefore can vary. The leads 18 couple to the IMD 10 using lead connectors 26, which are fixed in a non-conductive header material 28, which can comprise an epoxy for example.

As shown in the cross-section of FIG. 1C, the IMD 10 typically includes a printed circuit board (PCB) 30, along with various electronic components 32 mounted to the PCB 30, some of which are discussed subsequently. Two coils (more generally, antennas) are show in the IMD 10: a telemetry coil 34 used to transmit/receive data to/from an external controller (not shown); and a charging coil 36 for charging or recharging the IMD's battery 14 using an external charger.

Figure 2:
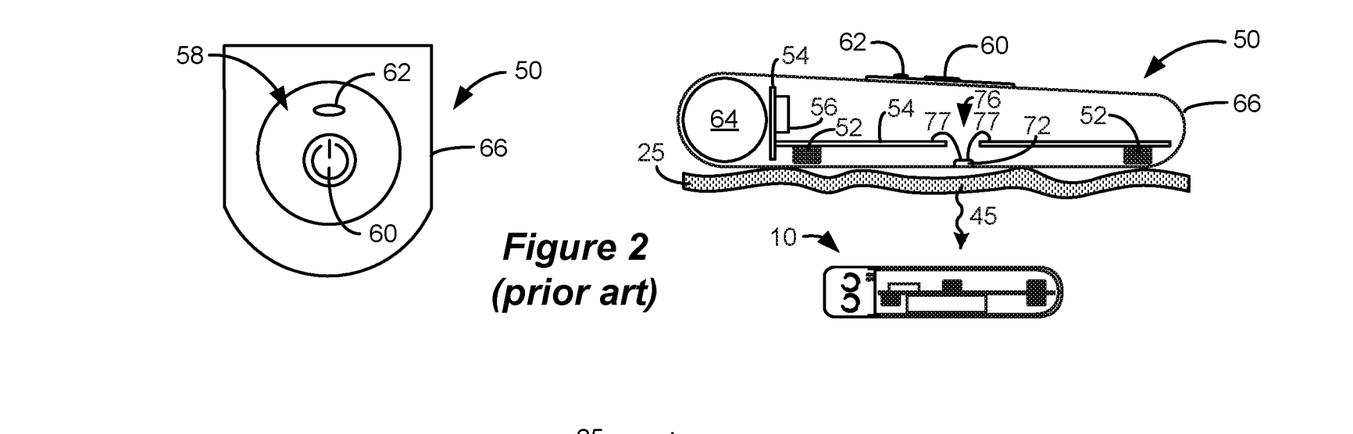

FIG. 2 shows an external charger 50 for the IMD 10 and shows the external charger 50 and IMD 10 in cross section with the external charger 50 wirelessly conveying power via a magnetic field 45 to the IMD 10, which power can be used to operate the IMD and/or recharge the IMD's battery 14. The magnetic field 45 is generated by a primary charging coil 52. The external charger 50 contains one or more PCB 54 on which electronic components 56 are placed. See U.S. Pat. No. 9,002,445. Some of these electronic components 56 are discussed subsequently. A user interface 58 including an on/off switch 60 allows a patient or clinician to operate the external charger 50 to start and stop generation of the magnetic field 45. User interface 58 may also include a Light Emitting Diode (LEDs) or other lamps and possibly also a speaker to indicate status. A battery 64 provides power for the external charger 50, which battery 64 may itself be rechargeable. The external charger 50 can also receive AC power from a wall plug. A hand-holdable housing 66 sized to fit a user's hand contains all of the components.

Figure 3:
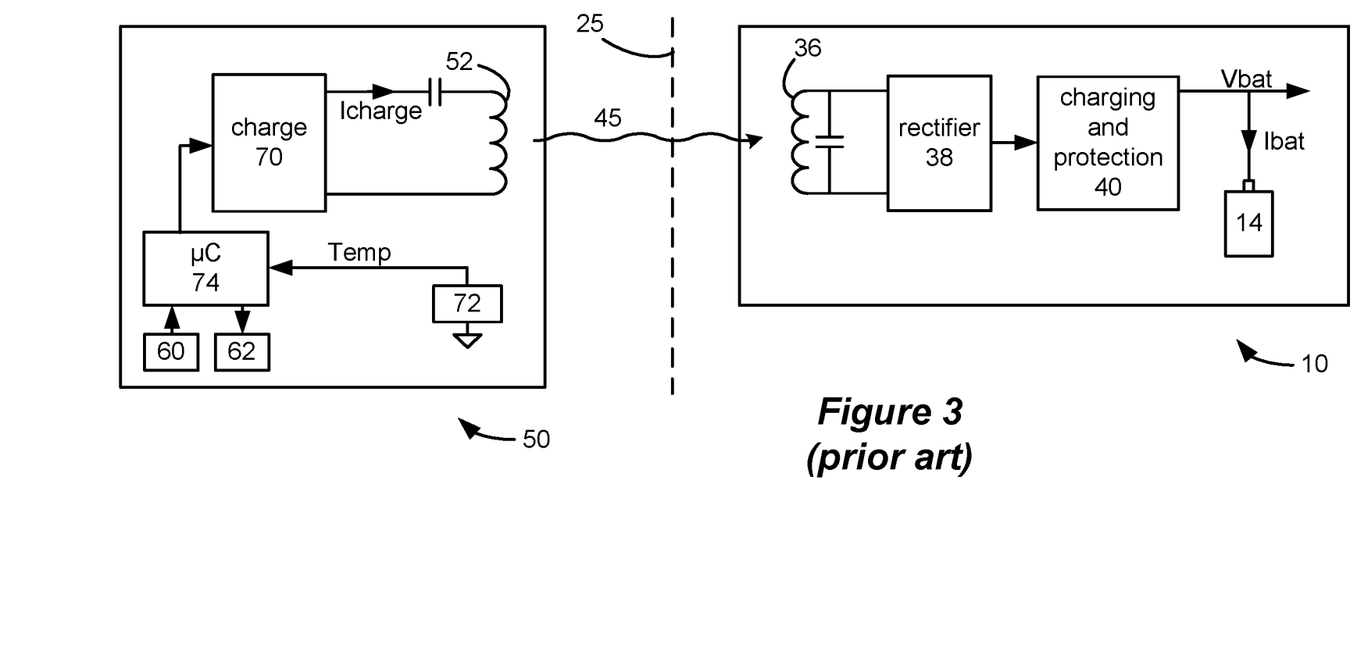
FIG. 3 shows circuitry in both, in accordance with the prior art.

Power transmission from the external charger 50 to the IMD 10 occurs wirelessly and transcutaneously through a patient's tissue 25 via inductive coupling. FIG. 3 shows details of the circuitry used to implement such functionality. Primary charging coil 52 in the external charger 50 is energized via charging circuit 70 with an AC current, Icharge, to create the AC magnetic field 45. This magnetic field 45 induces a current in the secondary charging coil 36 within the IMD 10, providing a voltage across coil 36 that is rectified (38) to DC levels and used to recharge the battery 14, perhaps via a battery charging and protection circuitry 40 as shown. The frequency of the magnetic field 66 can be perhaps 80 kHz or so. When charging the battery 14 in this manner, is it typical that the housing 66 of the external charger 50 touches the patient's tissue 25, perhaps with a charger holding device or the patient's clothing intervening, although this is not strictly necessary.

External charger 50 can also include one or more temperature sensors 72, such as thermistors or thermocouples, which can be used to report the temperature (Temp) of external charger 50 to its control circuitry 74. The measured temperature can in turn be used to control production of the magnetic field 45 such that the temperature remains within safe limits. This is important as the magnetic field 45 can induce Eddy current in conductive structures within the external charger 50, which Eddy currents in turn produce heat. Such heat generation carries a risk of aggravating the patient's tissue 25.

Figure 4:
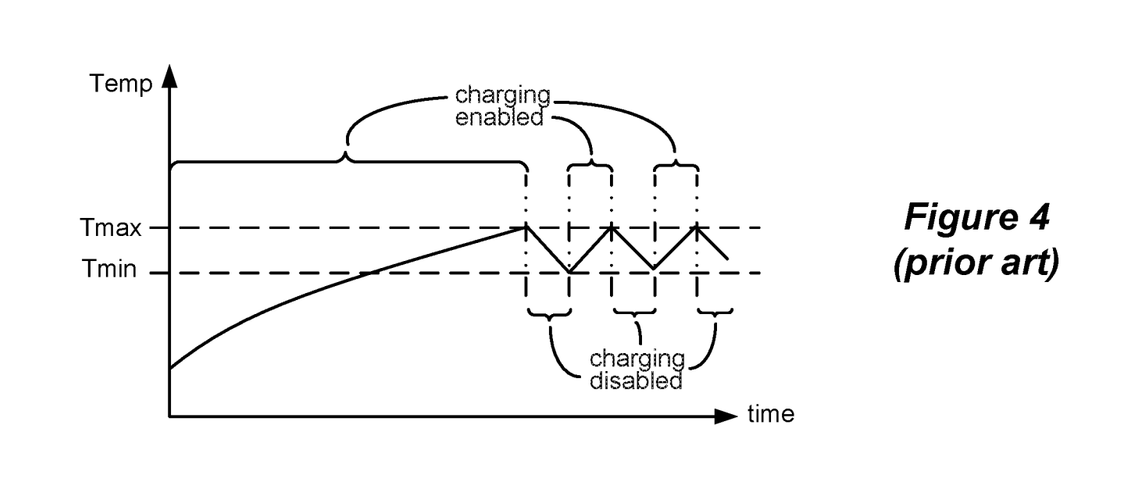
FIG. 4 shows how temperature can be controlled in the external charger of FIG. 2 by duty cycling the generated magnetic field.

Temperature control of the external charger 50 during an IMD charging session can occur for example as explained in U.S. Pat. No. 8,321,029, which is described here with respect to FIG. 4. As shown, a maximum temperature limit, Tmax, is set at which the external charger 50 will operate. Tmax is generally set in accordance with regulations designed to prevent tissue 25 aggravation, and may comprise 41° C. for example. When the external charger 50 is turned on (switch 60), Icharge flows through the primary charging coil 52, which produces the magnetic field 45, causing the temperature sensed by the temperature sensor 72 to increase. When Tmax is reached, the control circuitry 74 will disable further generation of the magnetic field 45 by stopping energizing of the primary charging coil 52 (i.e., Icharge=0). This causes the sensed temperature to decrease. Eventually, the temperature falls to a second temperature limit, Tmin, which may comprise 39° C. for example. At this minimum temperature, the control circuitry 74 can once again begin energizing the primary charging coil 52 with Icharge, once again producing the magnetic field 45 and causing the temperature to increase, etc. In this manner, during latter portions of the charging session when temperatures are higher, the charging coil 52 and magnetic field 45 are duty cycled on and off, thus keeping the temperature of the external charger 50 within a safe range between Tmax and Tmin.

In the example of FIG. 3, there is one temperature sensor 72 which is thermally adhered to an inside surface of the external charger 50's housing 66. In this design, lead wires 77 connect the temperature sensor 72 to the electronics (e.g., control circuitry 74) connected to the PCB 54, with lead wires 77 passing through a central hole 76 in the PCB 54.

BRIEF DESCRIPTION OF THE DRAWINGS

FIG. 2 shows an external charger being used to charge a battery in an IMD, while

FIGS. 6A and 6B show a top side of the circuit board in the charging coil assembly both with and without the thermal diffuser, while

DETAILED DESCRIPTION

The inventors see room for improvement in the external charger 50 described earlier, particularly as concerns thermal management.

First, because all electrical components and the charging coil 52 are enclosed in a single housing 66, certain conductive structures within the housing such the battery 64 and the electronic components 56 are in proximity to the charging coil 52 and the magnetic field 45 it generates. Eddy currents will thus be generated in these conductive structures in response to the magnetic field 45, which generates additional heat in the external charger 50. As a result, the external charger 50 will more readily approach its maximum temperature set point, Tmax, as sensed by temperature sensor 72. This limits generation of the magnetic field 45, and ultimately the power that can be delivered to the IMD 10, which limits the speed at which the IMD 10 can be charged.

Second, placement of the temperature sensor 72 on the inside surface of the housing 66 is difficult. Lead wires 77 are required to connect the temperature sensor 72 to the PCB 54, and these lead wires 77 are delicate and easily damaged or broken.

Third, while placement of the temperature sensor 72 is logical in that it attempts to sense the temperature of the external charger 50 at a position that is closest to the patient, the temperature generated by the external charger 50 is not highest at this position. Thus, the external charger 50 may actually experience temperatures that are higher than what the temperature sensor senses.

Figure 5A:
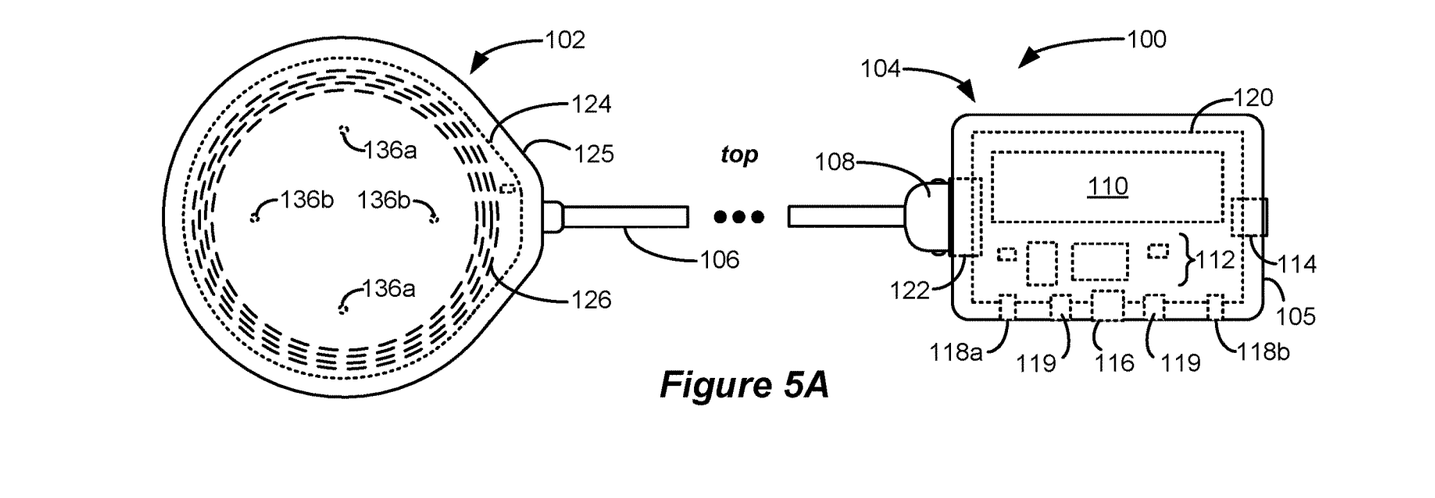
FIGS. 5A and 5B show a first example of an improved external charger system having an electronics module and charging coil assembly connected by a cable, in which a thermal diffuser is included within the charging coil assembly.
Figure 5B:
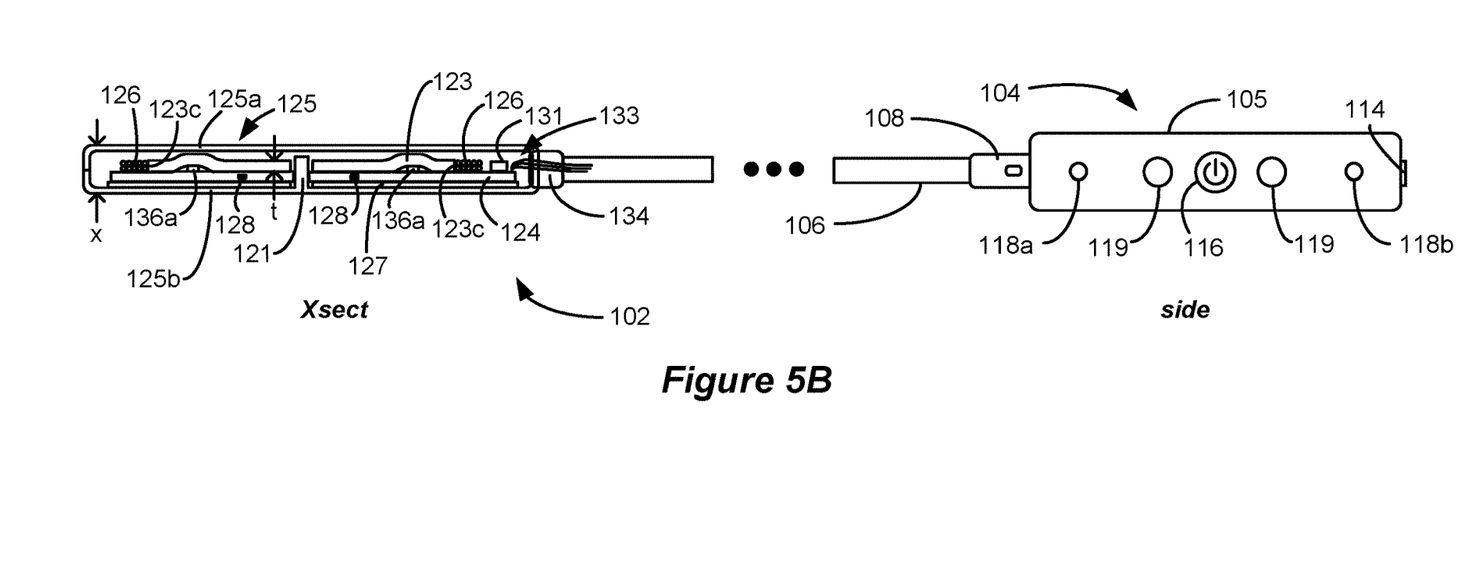

To address these concerns, an improved charging system 100 for an IMD 10 is shown in FIG. 5A in a plan view and in FIG. 5B in a side and cross sectional view. The charging system 100 is generally similar in structure to the charging system disclosed in U.S. Patent Application Publication 2017/0361113, but includes additional aspects related to thermal management.

Charging system 100 includes two main pieces: an electronics module 104 and a charging coil assembly 102 which includes a charging coil 126. The electronics module 104 and the charging coil assembly 102 are connected by a cable 106. The cable 106 may be separable from both the electronics module 104 and the charging coil assembly 102 via a port/connector arrangement, but as illustrated cable 106 is permanently affixed to the charging coil assembly 102. The other end of the cable 106 includes a connector 108 that can attach to and detach from a port 122 of the electronics module 104, although this end may be permanently affixed as well.

Electronics module 104 preferably includes within its housing 105 a battery 110 and active circuitry 112 needed for charging system operation, some of which are described subsequently with respect to FIG. 7. Electronics module 104 may further include a port 114 (e.g., a USB port) to allow its battery 110 to be recharged in conventional fashion, and/or to allow data to be read from or programmed into the electronics module, such as new operating software.

Housing 105 may also carry user interface elements, which as shown in the side view of FIG. 5B can include an on/off switch 116 to start/stop generation of the magnetic field 45 from the primary charging coil 126, and one or more indicators such as LEDs 118a, 118b, and 119. In one example, LED 118a is used to indicate the power status of the electronics module 104, i.e., the status (capacity) of the electronics module 104's battery 110 and whether it needs charging. LED 118b may similarly indicate the status of the battery 14 (FIG. 1C) in the IMD 10 being charged, which information may be telemetered from the IMD 10 to the charging coil assembly 102 in different manners, as explained in the above-referenced '113 Publication. One or more LEDs 119 may indicate the degree of coupling/alignment between the charging coil assembly 102 and the IMD 10 during a charging session, as explained further below. More complicated user interfaces, such as those incorporating a speaker and a display, could also be used. User interface elements can be included on other faces of the electronic module's housing 105, and may be placed such that they are easily viewed for the therapeutic application at hand (e.g., SCS, DBS).

Electronics are integrated within the housing 105 of the electronics module 104 by a circuit board 120. Active circuitry 112 may include control circuitry 150 for the charging system 100, as shown in FIG. 7. Control circuitry 150 can comprise a microcontroller programmed with firmware, such as any of the STM32L4 ARM series of microcontrollers provided by STMicroeletronics, Inc., as described at http://www.st.com/content/st_com/en/products/microcontrollers/stm32-32-bit-arm-cortex-mcus/stm3214-series.html?querycriteria=productId=SS1580. Control circuitry 150 may also comprise an FPGA, DSP, or other similar digital logic devices, or can comprise analog circuitry at least in part as explained further below. Control circuitry 150 can further comprise a memory programmed with firmware and accessible to a microcontroller or other digital logic device should that logic device not contain suitable on-chip memory.

Charging coil assembly 102 preferably contains only passive electronic components that are stimulated or read by active circuitry 112 within the electronics module 104. Such components include the primary charging coil 126 already mentioned, which as illustrated comprises a winding of copper wire and is energized by charging circuitry 152 (FIG. 7) in the electronics module 104 to create the magnetic field 45 that provides power to the IMD 10, such as may be used to recharge the IMD 10's battery 14. As shown in FIG. 5B, the primary charging coil 126 is mounted to the top side of a circuit board 124 within a housing 125 of the charging coil assembly 102. Housing 125 is preferably formed of a plastic material (e.g., polycarbonate) and as shown preferably comprises a top housing portion 125a and a bottom housing portion 125b, which may be joined during manufacturing by screwing, snap fitting, ultrasonic welding, or solvent bonding. Various views of the circuit board 124 with housing portions 125a and 125b removed for easier viewing are shown in FIGS. 6A-6D. One or more bosses 121 (FIG. 5B) may be formed in the bottom housing portion 125b to secure the circuit board 124 and other components, and thus the circuit board may include one or more holes that receive the one or more bosses. In FIGS. 6A-6D, a central hole 124a is provided in the circuit board 124 for receiving the central boss 121 shown in FIG. 5B. Top housing portion 125a may also have bosses or other stabilizing components, although this isn't shown. At least some aspects of active circuitry 112 may also appear in the charging coil assembly 102 if desired or convenient. Preferably, the user interface is associated only with housing 105 of the electronics module, and housing 125 of the charging coil assembly has no user interface elements associated with it.

Because the housing 125 of the charging coil assembly 102 is relatively thin—with a thickness x of 1.0 cm or less—and because the primary charging coil 126 is generally located at the center of this thickness, the magnetic field 45 generated by the primary charging coil 126 during a charging session will generally be the same on both sides of the assembly. Therefore, either the top 125a or bottom 125b housing portion may face the patient (and the IMD 10) during a charging session.

Charging coil assembly 102 preferably includes at least one tuning capacitor 131 mounted to the circuit board 124. Capacitor 131 is coupled to the charging coil 126 (see FIG. 7) to generally tune the resonant frequency of this L-C circuit (e.g., to 80 kHz). One skilled in the art will understand that the value of the capacitor 131 (C) connected to the charging coil 126 will be chosen depending on the inductance (L) of that coil, in accordance with the equation f(res)=1/sqrt(2πLC). Tuning capacitor 131 can be placed in series or in parallel with primary charging coil 126.

Figure 6A:
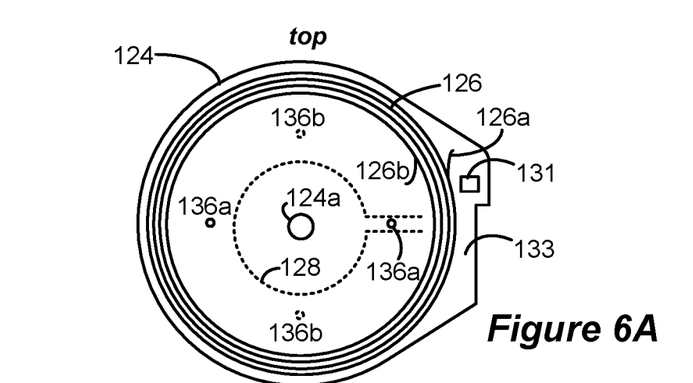
Figure 6B:
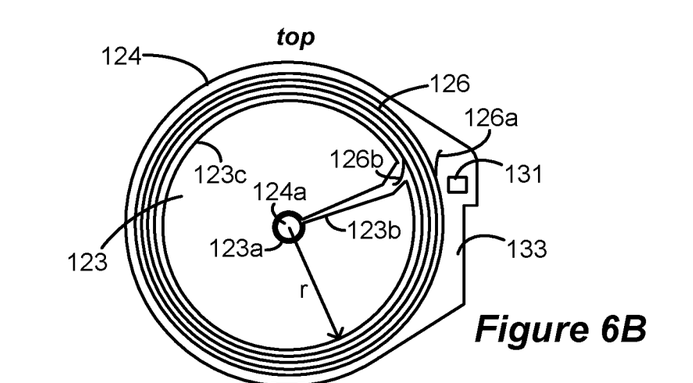
Figure 6C:
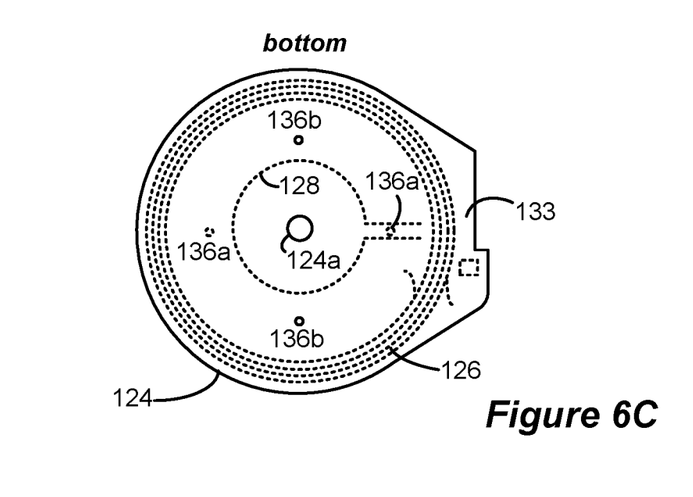
FIGS. 6C and 6D show the bottom side of the circuit board both with and without a thermally insulating material.

Also present in the charging coil assembly 102 are one or more temperature sensors, which are labeled 136a and 136b depending on whether such sensors are located on the top or bottom of the circuit board 124. As shown in FIGS. 5A, 6A and 6C, two temperature sensors 136a are present on the top of circuit board 124, and two temperature sensors 136b are present on the bottom of circuit board 124, with each spaced 90-degrees radially within primary charging coil 126. In other examples, temperature sensors may be present only on the top or only on the bottom of the circuit board 124. For example, only two temperature sensors 136a spaced at 180-degrees may be present on the top of the circuit board 124. The temperature sensors may comprise thermistors, and in one example can comprise TMP112 High-Accuracy, Low-Power, Digital Temperature Sensors With SMBus and Two-Wire Serial Interface in SOT563, manufactured by Texas Instruments, Inc.

The charging coil assembly 102 may also include one or more sense coils 128, as best shown in FIGS. 5B, 6A and 6C. As explained in the above-referenced '113 Publication, sense coil(s) 128 can be used to determine the alignment—e.g., the lateral offset—between the primary charging coil 126 in the charging coil assembly 102 and an IMD 10 being charged. During a charging session, some amount of energy in the magnetic field 45 produced by the primary charging coil 126 will couple to the sense coil(s) 128, and such coupling will be dependent on the positioning of the primary charging coil 126 relative to the IMD 10. Thus, as the '113 Publication teaches, one or more of a magnitude of signal induced in the sense coil(s) 128, a phase angle of the induced signal, and a resonant frequency of the charging system as determined using the induced signal, can be used to determine the alignment between the primary charging coil 126 and the IMD 10.

During a charging session, if the primary charging coil 126 is misaligned with the secondary charging coil 36 (FIG. 1B) in the IMD 10, this will reduce the coupling between these coils, and hence reduce the amount of energy the secondary charging coil 36 receives. This will in turn reduce the rate at which the IMD's battery 14 can be charged, or more generally can render the charging process inefficient. By contrast, when the primary charging coil 126 perfectly overlies the secondary charging coil 36 (FIG. 1B) in the IMD 10—such as when the central axes of coils 126 and 36 are collinear—the coupling will be high, and charging will be faster and more efficient. The degree of misalignment using measurements taken from the sense coil(s) 128 can be determined by the control circuitry 150 as explained further below, and indicated at LED(s) 119 to inform the patient whether he should try to move the charging coil assembly 102 relative to the IMD 10 to better improve coupling.

Sense coil(s) 128 are preferably within and concentric with the primary charging coil 126, and are preferably formed as traces within the circuit board 124. Although sense coil(s) 128 are illustrated as comprising a single turn, they may comprise a plurality of turns. Sense coil(s) 128 are preferably wound in a plane parallel to a plane in which the primary charging coil 126 is wound.

Cable 106 includes wires 134 that terminate in the charging coil assembly 102 at a circuit board contact portion 133, where the wires may be soldered onto contact pads or within vias in the circuit board 124. As shown in the circuit diagram of FIG. 7, such wires 134 include wires to carry differential AC current signals Icharge+ and Icharge− from charging circuitry 152 in the electronics module 104 to the primary charging coil 126 in the charging coil assembly 102 to energize the coil with an AC current. These wires are preferably Litz wires, which can pass the AC current from the charging circuitry 152 to the primary charging coil 126 with reduced loss.

Wires 134 also include those that carry temperature data from the temperature sensors to the electronics module 104. FIG. 7 shows two temperature sensors 136(1) and 136(2) present in the charging coil assembly 102 which report temperature data Temp1 and Temp2. As noted earlier, different numbers of temperature sensors can be used, and cable 106 can include extra wires 134 to accommodate additional temperature sensors if necessary. Temperature data may also be multiplexed on a single wire 134. Temperature data Temp1 and Temp2 may comprise either an analog voltage indicative of the temperature sensed by their respective temperature sensors 136(1) and 136(2), or may comprise digital data indicative of the sensed temperature. This will depend on the nature of the temperature sensors and whether they output analog or digital data. If the temperature data is analog, such data is preferably digitized before being presented to a thermal analysis module 156 in the electronics module 104. Digitization of the temperature data may occur using an A/D circuit, or A/D inputs of the control circuit 150 may be used if present. As shown, thermal analysis module 156 may comprise a portion of the control circuitry 150 of the electronics module 104, where it operates as firmware programmed into the control circuitry. Thermal analysis module 156 can also comprise analog circuitry in whole or in part.

Wires 134 within cable 106 may further include wires that carry differential voltage signals Va+ and Va− from the ends of the sense coil 128 in the charging coil assembly 102, which differential signals evidence the voltage Va induced on the sense coil and as useful to determining alignment as discussed earlier. As shown in FIG. 7, signals Va+ and Va− are reported to a position analysis module 154 present in the electronics module 104. Position analysis module 154 preferably comprises part of the control circuitry 150, and may comprise firmware programmed into the control circuitry 150. Signals Va+ and Va− are preferably digitized before being presented to the position analysis module 154, with digitization occurring using an A/D circuit, or A/D inputs of the control circuit 150 if present. As noted above and as discussed in detail in the above-referenced '113 Publication, the magnitude of Va, the phase of Va relative to a reference phase (such as the drive signal provided to the primary coil), and/or the resonant frequency of the charging system as determined by assessing Va, can be used by the position analysis module 154 to determine charger-to-IMD alignment. The determined alignment may then be indicated to a user via alignment indicator 119 discussed earlier. If more than one sense coil 128 is present in the charging coil assembly 102, additional wires 134 may be provided to report the voltage induced across such additional sense coils (Vb, Vc, etc.) to position analysis module 154.

As noted earlier, charging system 100 includes additional aspects to assist with thermal management. For example, as shown in FIG. 5B, the charging coil assembly 102 can include a thermal diffuser 123. In one example, the thermal diffuser 123 comprises a thermally conductive, soft plastic material. For example, the thermal diffuser may comprise an acrylic pad, such as a non-silicone acrylic pad, such as Part No. 5590H, manufactured by 3M, Inc. See http://multimedia.3m.com/mws/media/9201120/3mtm-thermally-conductive-acrylic-interface-pad-5590h.pdf. Thermal diffuser 123 preferably has a tacky surface allowing it to be pressed onto and adhered to the top of the circuit board 124 and any components on this top surface, including temperatures sensors 136a. Thermal diffuser 123 preferably has a high thermal conductivity of greater than 1.0 W/m-K, and more preferably about 3.0 W/m-K. Thermal diffuser 123 also preferably has low electrical conductivity, and may have a dielectric constant of about 5-6 in one example. Thermal diffuser 123 preferably has a thickness t greater than or equal to a thickness of the primary charging coil 126, which thickness t may range from 0.5 to 4.0 mm for example.

There is not a substantial amount of conductive structures proximate to the primary charging coil 126 in the design of the charging coil assembly 102, and thus it is not as subject to the generation of Eddy currents and heat as occurred in the prior art design discussed in the Introduction. This means that charging coil assembly 102 is able to generate higher power magnetic fields without overheating, e.g., without reaching a maximum prescribed temperature, Tmax. Thus, the IMD 10 can be charged faster and more efficiently by charging system 100.

The structure that generates the most heat in the charging coil assembly 102 is the primary charging coil 126 itself, which creates a hot ring-shaped area inside of the housing 125. Thermal diffuser 123 acts as a heat sink, and provides a heat transfer path away from the primary charging coil 126, thus distributing this heat over a larger circular area. Further, this distributed heat is directed to the temperature sensors 136a and/or 136b, and especially to temperature sensors 136a on the top of the circuit board which with the thermal diffuser 123 is in direct contact. As such, the temperature sensors are better able to accurately sense the temperature generated within the charging coil assembly 102. Further, because the temperature sensors 136a and 136b are mounted to the circuit board 124 in traditional fashion, lead wires (e.g., 77, FIG. 2) and complicated sensor mounting within the assembly 102 is not required as in the prior art design, which simplifies manufacturing and increases reliability.

To best distribute the primary charging coil 126's heat, it is preferred that the thermal diffuser 123 be in contact with the primary charging coil 126. As best seen in FIGS. 5B and 6B, such contact may occur at an outer edge 123c of the thermal diffuser 123, which edge 123c (of thickness t) is in contact with an inside edge of the primary charging coil 126, which has diameter r. Note that FIG. 6A shows the top of circuit board 124 without the thermal diffuser 123, while FIG. 6B shows the top with the material 123 in place.

An advantage to using a soft material for the thermal diffuser 123 is that it can be cut and shaped. For example, in FIG. 6B a hole 123a has been cut in the thermal diffuser 123 to accommodate passage of the central boss 121 (FIG. 5B). Further, a cut 123b has been made which spans from the hole 123a to the edge 123c of the thermal diffuser 123. This cut 123b can accommodate the termination 126b of the inner end of the primary charging coil 126 to the circuit board, which termination may not be covered by the thermal diffuser 123. Further, cut 123b allows the thermal diffuser 123's size to be adjusted slightly to bring the material into contact with the inner edge of diameter r of the primary charging coil 126. If due to manufacturing variation this inner edge diameter r is larger than usual, the cut 123b may be widened to increase the diameter of the thermal diffuser 123 to allow edge 123c to contact the inner edge; if inner edge diameter r is smaller, the cut 123b may be made smaller to decrease the diameter of the thermal diffuser 123 to allow edge 123c to fit within the inner edge.

While it is beneficial to have the thermal diffuser 123 in contact with the primary charging coil 126 to best assist in distributing its heat, this is not strictly necessary. Heat may conduct from the primary charging coil 126 to the thermal diffuser 123 even if they are not in direct contact, as the heat may be transferred by intermediaries, such as the circuit board 124 and the air within the charging coil assembly 102. In this regard, although not shown, the thermal diffuser 123 may be connected to one side of the circuit board 124 while the primary charging coil 126 is mounted to the other side.

Returning to FIG. 5B, the charging coil assembly 102 may include a thermally insulating material 127 on the bottom of the circuit board 124. In one example, the thermally insulating material 127 may comprise a foam material, such as a urethane foam, and more particularly may comprise a Poron™ urethane, manufactured by Rogers Corp. See https://www.rogerscorp.com/ems/poron/index.aspx. Thermally insulting material 127 serves different purposes. First, it can have tacky surfaces on both of its sides, which can adhere to the bottom side of the circuit board 124 and to the inside surface of the bottom housing portion 125b. This helps to stabilize the components within the charging coil assembly 102, and dampens mechanical shock to protect the charging coil assembly 102 from damage (e.g., if dropped).

Figure 6D:
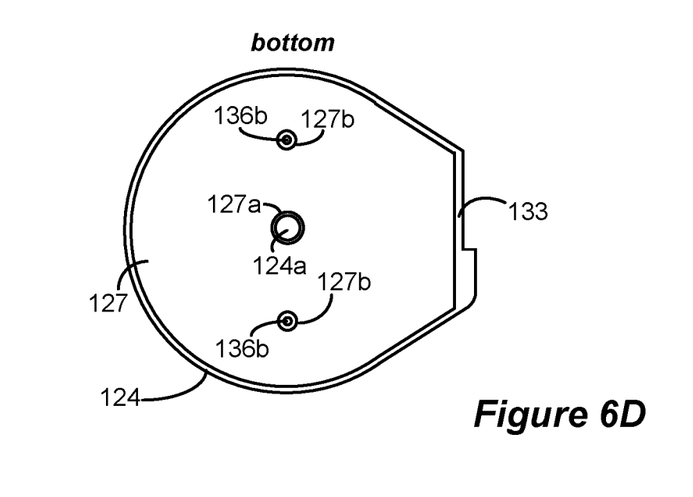

Second, the thermally insulating material 127 will prevent heat from the primary coil 126 and distributed by the thermal diffuser 123 from reaching the inside surface of the bottom housing portion 125b. If the bottom housing portion 125b faces the patient during a charging session, the thermally insulating material 127 will prevent heat from reaching the patient, which is preferred for safety reason. Preferably, the thermal conductivity of thermally insulating material 127 is 0.2 W/m-K or less. Note that FIG. 6C shows the bottom of circuit board 124 without the thermally insulating material 127, while FIG. 6D shows the bottom with the material 127 in place. Thermally insulating material 127 may be thinner than the thickness t of the thermal diffuser, and may be 1.5 mm or less.

If the charging coil assembly 102b includes temperature sensors 136b on the bottom side of the circuit board 124 as illustrated, holes 127b (FIG. 6D) can be provided in the thermally insulating material 127 through which the temperature sensors 136b emerge. This can help to distribute heat to these sensors 136b. Further, holes 127b allow the temperature sensors 136b to be brought into physical and thermal contact with the inner surface of bottom housing portion 125b. This can be useful, because—similarly to the prior art design of FIG. 2—these temperature sensors 136b will sense a temperature that is closest to the patient (assuming that portion 125b contacts the patient during a charging session). Having said this, use of sensors 136b on the bottom of the circuit board 124 is not strictly necessary, and thus holes 127b may not be necessary.

Figure 7:
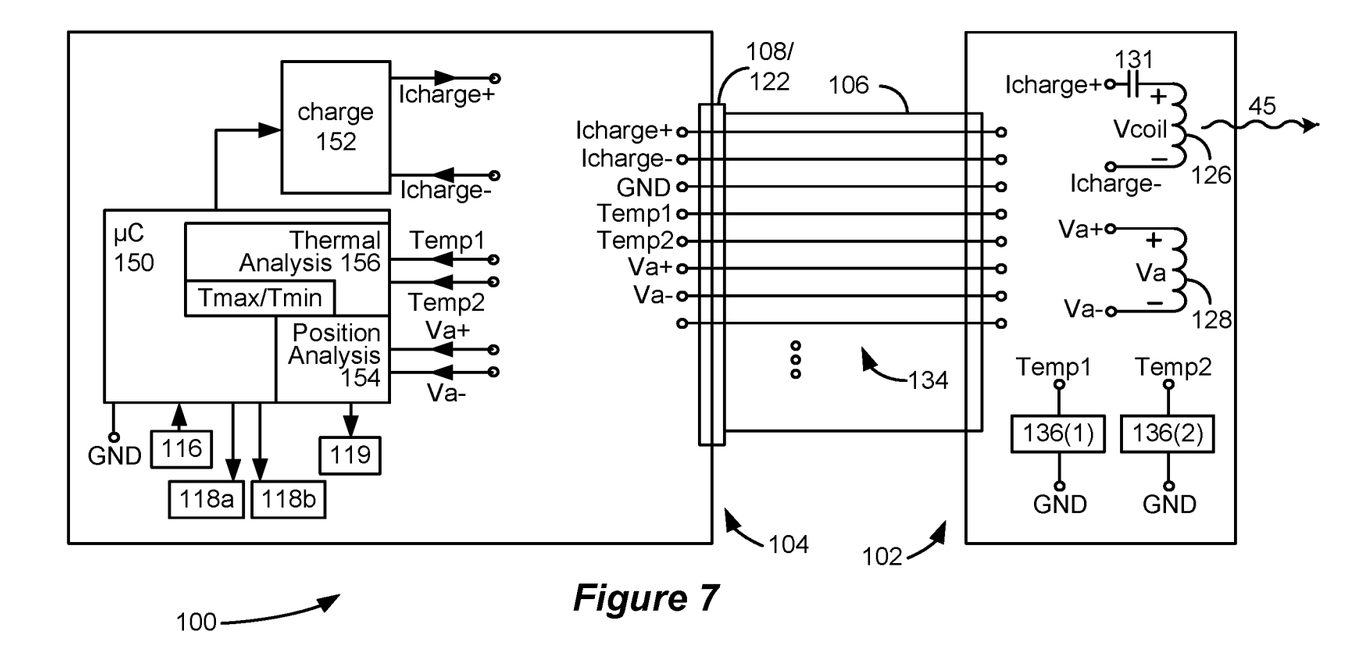
FIG. 7 shows circuitry within the external charger system.

Much of the circuitry of the charging system 100 depicted in FIG. 7 has already been discussed, but some extra comments are made here as regards thermal management and control of the system. As discussed earlier, temperature data (e.g., Temp1, Temp2, etc.) is preferably provided from the one or more temperature sensor 136 to the thermal analysis module 156 in the electronics module 104. If more than one temperature sensor is present, the thermal analysis module 156 can determine a single temperature indicative of the temperature of the charging coil assembly. Such single temperature can be for example the average of the reported temperature data from each sensor, or (more conservatively from a safety standpoint) the highest of the reported temperature data.

The single temperature may then be compared to Tmax and Tmin as stored in memory associated with the thermal analysis module 156 to control generation of the magnetic field 45. Such control may occur as described earlier with reference to FIG. 4, with the control circuitry 150 instructing the charging circuitry 152 to stop energizing the primary charging coil 126 when Tmax is reached (allowing the temperature to decrease), and instructing the charging circuitry 152 to again begin energizing the primary charging coil 126 when Tmin is reached (allowing the temperature to increase). Thus, as before, the charging coil 126 may be duty cycled on and off, thus keeping the temperature of the external charger 50 within a safe range between Tmax and Tmin. This is however just one example of control, and thermal analysis module 156 and control circuitry 150 more generally may control charging circuitry 152 to energize the primary charging coil 126 in different manners depending on the reported temperature.

Figure 8A:
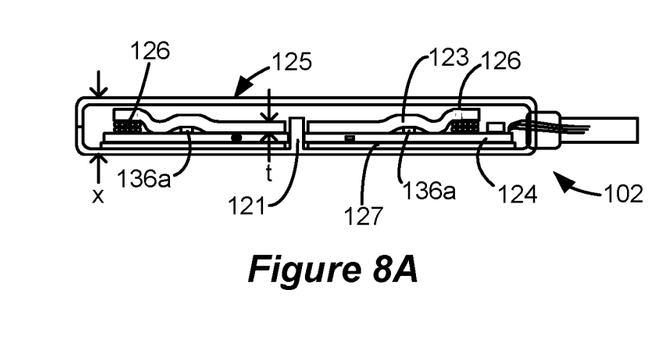
FIGS. 8A-8C show different examples of how the thermal diffuser may be positioned within the charging coil assembly.

Thermal diffuser 123 can be differently positioned in the charging coil assembly 102. For example, in FIG. 8A, the thermal diffuser 123 overlies and is in contact with the top of the primary charging coil 126. This configuration also helps to distribute heat from the primary charging coil 126 to the thermal diffuser 123. The thermal diffuser 123 may also be pressed to be in contact with the inner edge of the primary charging coil 126 as discussed earlier, and may also contact the outer edge of the primary charging coil, although this isn't illustrated. Note that the thickness x of the charging coil assembly 102 may need to be increased in this example to accommodate the additional thickness t of the thermal diffuser 123 on top of the primary charging coil 126.

Figure 8B:
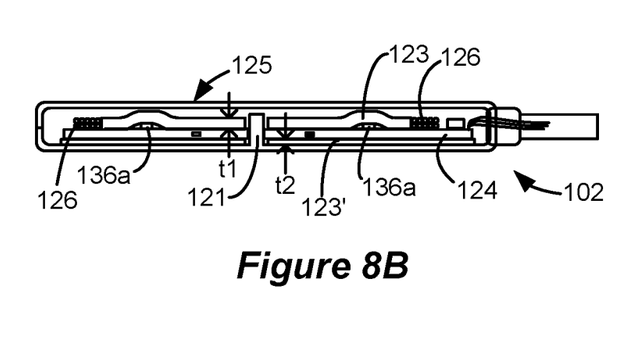

In FIG. 8B, a second thermal diffuser 123' has been added to the bottom of the circuit board 124. This second thermal diffuser 123' may take the place of the thermally insulating material 127 as shown in FIG. 8B, or may occur between the circuit board 124 and the thermally insulating material 127 (not shown). Use of a second thermal diffuser 123' assists in further distributing heat away from the primary charging coil 126 and towards the temperature sensors, in particular sensors 136b residing on the bottom of the circuit board 124. If a thermally insulating material 127 isn't used, consideration may need to given to whether the second thermal diffuser 123' should be in contact with the inside surface of the bottom housing portion 125b; if in contact with the inside surface, heat will also be transmitted to the bottom housing portion 125b and also to the patient, which may or may not be tolerable. Thermal diffusers 123 and 123' may have the same thickness, or different thicknesses (t1, t2) as shown.

Figure 8C:
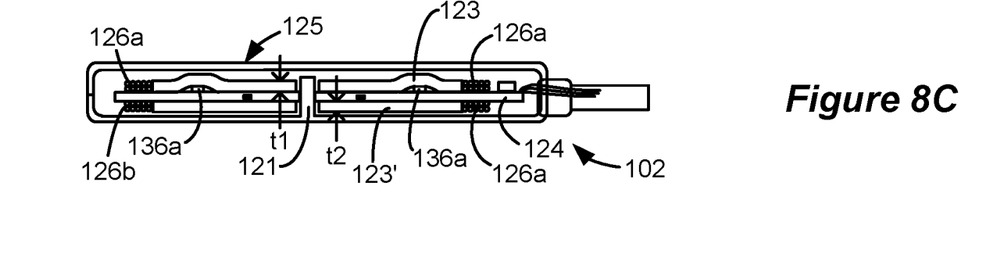

FIG. 8C show a modification involving a split primary charging coil having two portions: a portion 126a on the top of the circuit board 124, and a portion 126b on the bottom of the circuit board. Such a split coil is explained in detail in U.S. Patent Application Publication 2017/0361111. Briefly, the coil portions 126a and 126b are connected in series via the circuit board 124, and so in effect operate similarly to the single primary charging coil 126 described earlier to generate a magnetic field 45. However, by virtue of the manner in which the coil portions 126a and 126b are wound and terminated at the circuit board 124, the magnetic field 45 produced has improved radial symmetry and uniformity. In any event, a thermal diffuser may be included with both coil portions, and as shown a top thermal diffuser 123 is included with top coil portion 126a, and a bottom thermal diffuser 123' is included with bottom coil portion 126b. Any of the modifications described earlier may be used with the design of FIG. 8C: for example, one or more thermally insulating materials 127 may be used (e.g., with one on the top and one on the bottom); the thermal diffusers 123 and 123' may overlie the coil portions 126a and 126b; etc.

Figure 9:
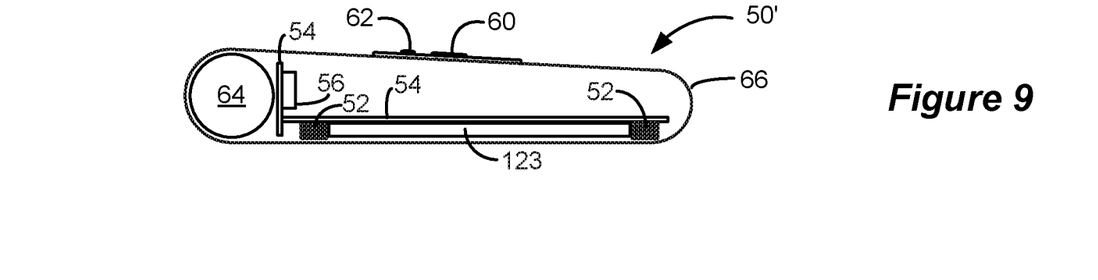
FIG. 9 shows use of the thermal diffuser in an external charger in which electronics and the primary charging coil are integrated within a single housing.

The charging system 100 employing a thermal diffuser has been illustrated so far in the context of a two-piece charger system having an electronics module 104 and charging coil assembly 102 in separate housings 105 and 125. However, a thermal diffuser may be used in an integrated external charger design in which all electronics and the primary charging coil are integrated within a single housing. For example, FIG. 9 shows the inclusion of a thermal diffuser 123 in an integrated external charger 50' similar to that described earlier in the Introduction. In this example, the primary charging coil 52 occurs on the bottom of the circuit board 124 as does the thermal diffuser 123, but either or both could appear on the top side as well. Although not illustrated, any of the modifications described earlier may be used with the design of FIG. 9.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover equivalents that may fall within the spirit and scope of the present invention as defined by the claims.

What is claimed is:

1. An external charger system for an implantable medical device, the external charger system comprising:
   a circuit board;
   a primary charging coil mounted to a first side of the circuit board, wherein the primary charging coil, when energized, is configured to generate a magnetic field to be received at the implantable medical device; and
   a thermal diffuser adhered to the first side of the circuit board and within the primary charging coil, wherein the thermal diffuser is configured to conduct heat away from the primary charging coil.

2. The external charger system of claim 1, wherein the thermal diffuser is further in contact with at least a portion of the primary charging coil.

3. The external charger system of claim 2, wherein the primary coil has an inner edge, and wherein the thermal diffuser has an outer edge in contact with the inner edge.

4. The external charger system of claim 1, further comprising a thermally insulating material in contact with a second side of the circuit board.

5. The external charger system of claim 1, further comprising at least one temperature sensor mounted to the circuit board.

6. The external charger system of claim 5, wherein the thermal diffuser is in contact with at least one of the temperature sensors.

7. The external charger system of claim 1, further comprising a first housing, wherein the circuit board, the primary charging coil, and the thermal diffuser are within the first housing.

8. The external charger system of claim 7, further comprising a second housing coupled to the first housing by a cable, wherein the second housing comprises charging circuitry configured to energize the primary charging coil via the cable to generate the magnetic field.

9. The external charger system of claim 8, further comprising at least one temperature sensor mounted to the circuit board, wherein each temperature sensor is configured to provide, via the cable, temperature data to control circuitry in the second housing, wherein the control circuitry is configured to use the temperature data to control generation of the magnetic field.

10. The external charger system of claim 1, wherein the thermal diffuser is adhered to the first side of the circuit board using a tacky surface of the thermal diffuser.

11. The external charger system of claim 8, further comprising a user interface associated with the second housing, wherein no user interface elements are associated with the first housing.

12. The external charger system of claim 1, wherein the thermal diffuser comprises a plastic material.

13. The external charger system of claim 12, wherein the thermal diffuser comprises an acrylic material.

14. The external charger system of claim 1, further comprising at least one sense coil within and concentric with the primary charging coil, wherein a signal induced in each sense coil is configured to provide information relevant to alignment of the primary charging coil with the implantable medical device during generation of the magnetic field.

15. An external charger system for an implantable medical device, the external charger system comprising:
    a first housing, in which comprises:
      a circuit board;
      a primary charging coil mounted to the circuit board, wherein the primary charging coil, when energized, is configured to generate a magnetic field to be received at the implantable medical device;
      at least one temperature sensor mounted to the circuit board and each configured to provide temperature data; and
      a thermal diffuser adhered to the primary charging coil and the at least one temperature sensor.

16. The external charger system of claim 15, wherein the primary charging coil and at least one of the temperature sensors are mounted to a first side of the circuit board, and wherein the thermal diffuser is further adhered to the first side of the circuit board.

17. The external charger system of claim 15, wherein the thermal diffuser is adhered to the primary charging coil and the at least one temperature sensor using a tacky surface of the thermal diffuser.

18. The external charger system of claim 15, further comprising a second housing coupled to the first housing by a cable, wherein the second housing comprises charging circuitry configured to energize the primary charging coil via the cable to generate the magnetic field, wherein the second housing further comprises control circuitry, wherein the control circuitry is configured to receive, via the cable, the temperature data and to control generation of the magnetic field using the temperature data.

19. The external charger system of claim 15, wherein the thermal diffuser comprises a plastic material.

20. The external charger system of claim 19, wherein the thermal diffuser comprises an acrylic material.

* * * * *